United States Patent [19]

Halpern

[11] Patent Number: 4,676,257

[45] Date of Patent: Jun. 30, 1987

[54] DENTAL ANESTHESIA APPARATUS

[75] Inventor: Gregory J. Halpern, Vernon Hills, Ill.

[73] Assignee: Pain Prevention, Inc., Wilmette, Ill.

[21] Appl. No.: 684,127

[22] Filed: Dec. 20, 1984

[51] Int. Cl.⁴ .............................................. A61N 1/04
[52] U.S. Cl. ................................ 128/787; 128/419 R; 128/803
[58] Field of Search ....... 128/303.13, 419 R, 421–423, 128/639, 644, 783, 787, 803

[56] References Cited

U.S. PATENT DOCUMENTS

| | | | |
|---|---|---|---|
| 1,585,795 | 5/1926 | Speter | 128/803 |
| 2,771,554 | 11/1956 | Gratzl | 128/421 |
| 2,949,107 | 8/1960 | Ziegler | 128/419 R |
| 2,986,140 | 5/1961 | Gardner et al. | 128/1 R |
| 3,213,851 | 10/1965 | Currea | 128/1 R |
| 3,677,268 | 7/1972 | Reeves | 128/803 |
| 3,791,373 | 2/1974 | Winkler et al. | 128/422 |
| 3,908,669 | 9/1975 | Man et al. | 128/422 |
| 4,109,660 | 8/1978 | Nesmeyanov et al. | 128/419 R |
| 4,215,698 | 8/1980 | Nuwayser | 128/803 |
| 4,390,023 | 6/1983 | Rise | 128/421 |
| 4,392,496 | 7/1983 | Stanton | 128/423 W |
| 4,411,277 | 10/1983 | Dickhudt | 128/784 |
| 4,431,000 | 2/1984 | Butler et al. | 128/421 |
| 4,483,338 | 11/1984 | Bloom et al. | 128/303.13 |
| 4,550,733 | 11/1985 | Liss et al. | 128/421 |

FOREIGN PATENT DOCUMENTS

| | | | |
|---|---|---|---|
| 722474 | 3/1932 | France | 128/423 |
| 348958 | 3/1937 | Italy | 128/422 |
| 498527 | 1/1939 | United Kingdom | 128/803 |

OTHER PUBLICATIONS

Cameron, "Diagnosis by Transillumination", 1924, p. 54.

Primary Examiner—William E. Kamm
Attorney, Agent, or Firm—Dick and Harris

[57] ABSTRACT

A dental anesthesia apparatus for utilization and cooperation with transcutaneous electrical nerve stimulation equipment which equipment generates low-energy electrical impulse waves to relieve pain. The apparatus includes connection members for electrical attachment to the wave generation equipment as well as provides remote switching controls to control the intensity of the generated wave being transmitted to the affected dental area. Through the remote control apparatus, the patient or the dentist himself is able to respond immediately to variations in pain to appropriately increase or decrease the intensity of the generated wave, as needed, to anesthetize the region from which the pain originates. Stainless steel electrode elements transmit the controlled impulse wave into electrode isolation media for retransmission of the generated wave through electrical conducting electrolyte solution impregnating the isolation media—all towards conducting of the desired wave output to the actual tissue area of a patient undergoing dental procedures.

16 Claims, 2 Drawing Figures

DENTAL ANESTHESIA APPARATUS

BACKGROUND OF THE INVENTION

The present invention relates in general to medical anesthesia apparata and particularly to a dental anesthesia apparatus for use with transcutaneous electrical nerve stimulation (TENS) equipment for generating and transmitting anesthetic electrical impulse waves to a patient's mouth for use in dental operations and procedures.

While the development and utilization of wave generation equipment for use as anesthesia and/or for reducing pain to muscular tissue has occurred over the last several decades, only lately has there been the introduction of TENS equipment capable of generating relatively new waveforms which more effectively relieve pain and/or increase the pain threshold in an individual or animal. One such example of TENS equipment for pain relief, capable of generating an "H-wave", is disclosed in now abandoned patent application Ser. No. 06/243,892.

Certainly, controls for altering the frequency and/or intensity of such generated waves on such TENS equipment have existed in the past. But few if any of the wave transmission devices have utilized the remote controlling of generated wave intensity, so as to permit immediate variation (increases or decreases) in wave generation intensity in immediate response to the pain being experienced, by, for example, the patient. Moreover, few of any of the prior art devices have addressed specific transmission and localization of the generated wave for use as an anesthetic in the potentially hazardous electrical-conducting region of the internal mouth.

It is accordingly an object of the present invention to provide a dental anesthetic module for use in association with wave generation equipment which safely and effectively transmits generated impulse waves from TENS equipment for particular use in a dental patient's mouth.

It is additionally an object of the present invention to provide such transmission means for utilization in a dental patient's mouth, of such a construction which precludes contact with electrical conducting portions of the transmission circuit with the electrically conducting environment manifested by a patient's mouth and to reduce shorts, burns and discomfort associated therewith.

As a further object of the present invention, is the provision of wave transmission means for directing the generated electrical impulse wave from transcutaneous electrical nerve stimulation equipment which transmission means possesses remote intensity control means to permit a patient and/or dentist to increase or decrease the intensity of the transmitted wave in immediate and direct response to the extent of pain being experienced by the patient and accordingly, to preclude the need for controlling intensity directly from the TENS equipment itself.

A further object of the invention includes a provision of such a wave generation apparatus which is inexpensive to manufacture which, at the same time, is easy to connect into existing TENS equipment through facilitated "jacking" techniques, while being capable of having the elements coming into contact with the patient's mouth withstand the effects of sterilization through conventional autoclave techniques.

As an additional object of the invention is the provision of such a dental apparatus for transmission of TENS equipment wave impulses which apparatus possesses, on the remote control portion, dial scale and/or light indicia means capable of disclosing to the patient or dentist the extent of intensity of waveform being transmitted to the dental procedure and into the mouth.

These and other objects of the invention will become apparent in light of the present specification and drawings.

SUMMARY OF THE INVENTION

The present invention comprises a dental anesthesia apparatus for use with transcutaneous electrical nerve stimulation equipment wherein said equipment is capable of generating a low energy electrical impulse wave. The waveform is directly transmitted by the dental anesthesia apparatus to the tissues and organs of mammals in order to lessen discomfort and relieve pain arising from dental problems and dental procedures directed thereto. The dental anesthesia apparatus is directed for use with such transcutaneous electrical nerve stimulation equipment of the kind possessing a wave generation means to produce the desired waveform, wave control means for independently varying the frequency of the generated waveform and a wave output means to accept, in a facilitated manner, the electrical connection of the dental anesthesia apparatus. In conducting the waveform to the area of tissue or organ to be anesthetized, the present dental anesthesia apparatus provides direct control over the intensity of the waveform being conducted.

Apparatus connection means are provided for operably and electrically connecting the dental anesthesia apparatus to the transcutaneous electrical nerve stimulation equipment. A first end of the apparatus connection means is operably and electrically connected to the wave output means of the transcutaneous electrical nerve stimulation equipment thereby serving to conduct the waveform produced by the wave generation means to the dental anesthesia apparatus. Incoming lead means are provided having a first end and a second end with the first end operably and electrically connected to the second end of the apparatus connection means. The incoming lead means serves to additionally operably conduct the waveform produced by the TENS equipment to said dental anesthesia apparatus. Incoming connector means are provided having a first end and a second end with the first end operably and electrically connected to the second end of the incoming lead means. The second end of the incoming connector means is operably and electrically attached to an internal circuit control means. The internal circuit control means is capable of electrically controlling, at a location remote to the TENS equipment, the intensity of the waveform produced by the wave generation means being conducted through the dental anesthesia apparatus. An outgoing connector means is provided having a first end and a second end, with the first end operably and electrically connected to the second end of the internal circuit means. Remote control housing means further operably contains the incoming connector means, the outgoing connector means, and the internal circuit control means.

Outgoing lead means extend from the remote control circuit and possess a first end and a second end, wherein said first end is operably and electrically connected to the outgoing connector means for further conducting the waveform as controlled by the internal circuit means. The second end of the outgoing lead means is operably and electrically connected to the electrode connector means. Electrode means are operably and electrically connected to the electrode connector means to enable the electrode means to be positioned in the mammal's mouth during the dental procedure and for conducting the controlled waveform and dispersing the waveform to the area of tissue or organ to be anesthetized. Electrode isolation means are provided for isolating the electrode means in order to prevent the electrode means from directly contacting the tissue or organ to be anesthetized or the mammal's teeth. Additionally, electrolyte means are impregnated into the electrode isolation means for effectively dispersing the waveform energy to the tissue or organ to be anesthetized.

In the preferred embodiment, the apparatus connection means comprises a pair of single conductor male banana jack connectors for the facilitated telescopic and electrical connection of the first end of the incoming lead means with the wave output connector means of the transcutaneous electrical nerve stimulation equipment wherein the wave output means consists of corresponding single conductor female banana jack connectors. The incoming lead means preferably comprise a pair of single conductor insulated wires for conducting the waveform generated by the wave generation means of the transcutaneous electrical nerve stimulation equipment to the dental anesthesia apparatus. The incoming lead means are of such a length so as to permit the manual operation of internal circuit control means by an individual proximate to said dental procedure, adjusting the intensity of the waveform and corresponding anesthetic affect, remote from the transcutaneous electrical nerve stimulation equipment. This adjustment may be made continually throughout the course of the dental procedure by either the individual performing the dental procedure or the patient. The incoming connector means, in this preferred embodiment, comprises a pair of single conductor male and female banana jack connector assemblies for the facilitated telescopic and electrical receipt of the second end of the incoming lead means and associated male banana jack connector in order to operably and electrically conduct said waveform generated by the wave generation means to the internal circuit control means.

The preferred embodiment further includes an internal circuit control means in the form of a 0-250 ohm rheostat element connected in series between one of the incoming connector means and one of the outgoing connector means, and a conductor element connected in series, creating a short circuit between the other of the incoming connector means and the other of the output connector means. The internal circuit control means thus serves to electrically control the intensity and corresponding anesthetic affect of the waveform being conducted through the apparatus to the patient's mouth. The internal circuit control means further includes a knob by which the rheostat element can be controlled so as to vary the resistance of the rheostat element. An indicator scale is also attached to the exterior of the remote control housing means adjacent to the knob for referencing the position of the knob itself.

Preferably, the outgoing connector means comprises a single two conductor male and female sub-minature phone jack connector assembly for the facilitated telescopic and electrical connection of the internal circuit means to the outgoing lead means. The outgoing lead means comprises a pair of single conductor cords having the single two conductor male sub-minature phone jack connector portion of the assembly operably and electrically attached to the first end of the outgoing lead means for the facilitated telescopic and electrical connection with the corresponding two conductor female sub-minature phone jack connector of the assembly, thereby serving to conduct the adjusted waveform to the electrode connection means.

In the preferred embodiment of the invention, the outgoing lead means are fabricated of biomedical wire having a non-toxic Teflon insulation coating capable of undergoing autoclave sterilization without decomposition. Furthermore, the electrode connector means comprise socket means operably and electrically attached to each conductor of the second end of the outgoing lead means. The electrode connector means operably receive and electrically connect the outgoing leads to the electrode means to conduct the controlled waveform to the area of tissue or organ to be anesthetized. The electrode connector means further includes an insulating sleeve covering each of the sockets so as to prevent each socket from contacting the tissue or organ to be anesthetized, or the patient's teeth. In this preferred embodiment, the insulating sleeve is formed of a heat shrinkable Teflon tubing material and the socket means are composed of a coiled spring assembly capable of restrainably retaining the electrode means and alternately permitting the removal and replacement of the electrode means.

The electrodes in the preferred embodiment, are formed of tapered stainless steel elements for conducting the waveform as controlled by the internal circuit control for dispersing the controlled waveform to the area of tissue or organ to be anesthetized. In one embodiment, these tapered stainless steel elements further include barbs operably attached so as to retain the electrode insulation means.

The electrode isolation means operably receive the tapered stainless steel elements, with said electrode isolation means being held in place about the tappered stainless steel elements by friction or the above described barbs to isolate the stainless steel elements and prevent their direct contact with the tissue or organ to be anesthetized, further serving to hold the tapered stainless steel elements in place during the dental procedure. The electrode isolation means are dimensioned so as to enable the tapered stainless steel elements to be fully inserted into the electrode isolation element, leaving no portion of the steel electrode exposed.

In the preferred embodiment of the invention the electrode isolation means is formed of an absorbant sponge-like material. This electrode isolation member is impregnated with an electrolyte means which, in one embodiment may comprise an electrode gel which, upon impregnation, serves to promote the conductivity of the electrode isolation means so as to promote the conduction and dispersion of the waveform energy to the tissues or organs to be anesthetized.

In one embodiment of the invention, the dental anesthesia apparatus further includes a visual indicator means comprising a light emitting diode element which is attached to the internal circuit control means. The degree of brightness of this light emitting diode varies with the intensity of the waveform being conducted through the internal circuit means thereby giving an additional visual indication of the intensity of the waveform, and corresponding anesthetic affect.

DETAILED DESCRIPTION OF THE DRAWINGS

Figure 1:
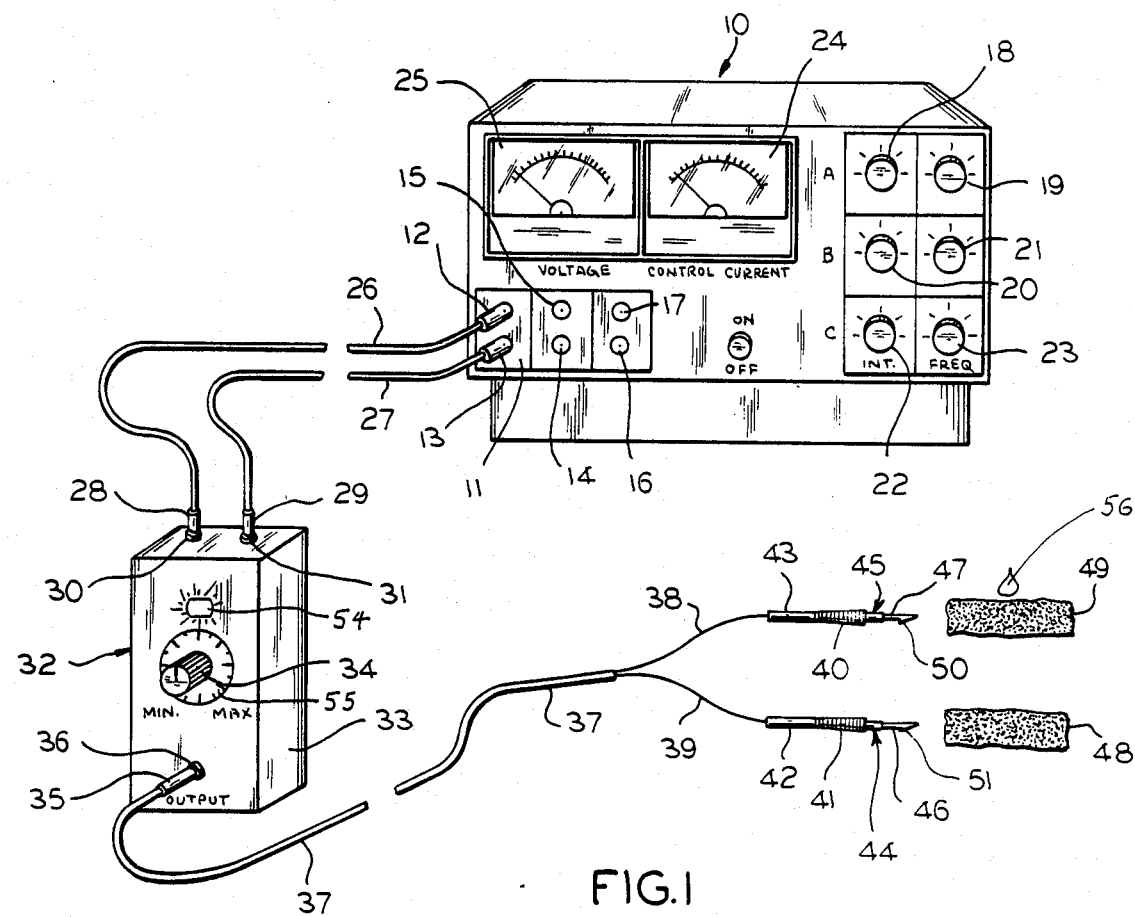
FIG. 1 of the drawings is a front perspective view of a transcutaneous electrical nerve stimulator wave generator together with the present dental anesthesia apparatus, shown connected to the transcutaneous electrical nerve stimulation equipment.

While this invention is susceptible of embodiment in many different forms, there is shown in the drawings and will herein be described in detail, several specific embodiments, with the understanding that the present disclosure is to be considered as an exemplification of the principles of the invention and is not intended to limit the invention to the embodiment illustrated.

The conventional transcutaneous electrical nerve stimulation equipment 10 capable of generating the desired low-energy electrical impulse waveform for cooperation with applicant's present dental anesthesia apparatus is shown in FIG. 1. Included within its outer housing are wave generation means for generating the desired waveform. The particular version of the transcutaneous electrical nerve stimulation equipment 10 illustrated is capable of generating the desired waveform on three separate output channels A, B and C. The intensity and frequency of the waveform generated on each channel A, B and C, are independently adjustable using intensity controls 18, 20 and 22, and frequency controls 19, 21 and 23, respectively.

The TENS equipment illustrated includes wave output means for each of the three channels A, B and C. Dental anesthesia apparatus 32 is also shown operably and electrically attached to the transcutaneous electrical nerve stimulation equipment 10 in FIG. 1. Specifically, the first end of apparatus connection means 12 and 13 are shown operably and electrically connected to wave output means 11. Apparatus connection means 12 and 13 each consists of a single conductor male banana jack connector which is mated with the respective corresponding single conductor female banana jack connectors of wave output means 11. The second end of apparatus connection means 12 and 13 are each operably and electrically connected to incoming leads 26 and 27. Incoming leads 26 and 27 are shown comprising a pair of single insulated conductor cords which connect dental anesthesia apparatus 32 to the transcutaneous electrical nerve stimulation equipment 10. Incoming leads 26 and 27 further serve to conduct the waveform generated by the wave generation means from the wave output means 11 to the dental anesthesia apparatus 32.

The second ends of each incoming leads 26 and 27 are operably and electrically connected to incoming connectors 28-31 which comprise a pair of single conductor male and female banana jack connector assemblies. The second ends of incoming lead means 26 and 27 are attached to the male portion of the banana jack connector assembly 28 and 29. The female portion of the single conductor banana jack assembly 30 and 31 are operably and electrically connected to the incoming circuit control means, a schematic diagram of which appears in FIG. 2, which control means are contained within remote control apparatus housing 33.

The second end of the internal circuit control means is operably and electrically connected to outgoing connectors 35 and 36. Outgoing connectors 35 and 36 comprise a single two conductor male and female sub-minature phone jack connector assembly. This second end of the internal circuit control means is attached to the female portion of the sub-minature phone jack connector assembly 36. The male portion of the sub-minature phone jack connector assembly 35 is operably and electrically attached to the first end of outgoing lead 37 which preferably comprises a pair of single conductor biomedical wires 38 and 39, each having a non-toxic Teflon insulation coating. The second end of outgoing lead 37 is operably and electrically connected to electrode connector assemblies 44 and 45. Electrode connectors 44 and 45 each comprise a socket 40 and 41 operably and electrically attached to each conductor of the outgoing leads 38 and 39. Sockets 40 and 41 of electrode connectors 44 and 45 receive and electrically connect outgoing lead 37 to electrodes 46 and 47. Electrode connector assemblies 44 and 45 further include an insulating sleeves 42 and 43 respectively, which cover sockets 40 and 41 thereby preventing the sockets 40 and 41 from directly contacting with the tissue or organ to be anesthetized, or, for that matter, the patient's teeth. As illustrated, insulating sleeves 43 and 42 are preferably formed of a heat shrinkable Teflon tubing material.

Sockets 40 and 41 are composed of a coiled spring assembly which is capable of restrainably retaining the electrodes 47 and 46 respectively, and alternately permits the removal and replacement of electrodes 47 and 46 for their sterilization or disposal. Electrodes 46 and 47 preferably comprise tapered stainless steel elements for conducting the waveform as controlled by the internal circuit control means and dispersing the waveform to the area of tissue or organ to be anesthetized. These tapered stainless steel elements may further include barbs 51 and 50 operably attached so as to retain the position of the steel elements within the electrode isolation means 48 and 49, respectively.

In this preferred embodiment, electrodes 46 and 47 are telescopically inserted into the center of the electrode isolation means 48 and 49. Electrode isolating means 48 and 49 respectively isolate the stainless steel elements 46 and 47 so as to prevent their direct contact with the tissue or organ to be anesthetized or the patient's teeth. Electrode isolation means 48 and 49 further serve to hold the tapered stainless steel elements 46 and 47 in place during the dental procedure, and are dimensioned to enable the tapered stainless steel elements 46 and 47 to be fully inserted into each, respectively, so as to leave no portion of the stainless steel elements 46 and 47 exposed which could possibly contact with the tissue, organ or teeth.

As illustrated in FIG. 1, electrode isolation means 48 and 49 are preferably formed of an absorbant sponge material. Furthermore, these electrode isolation means 48 and 49 are impregnated with an electrolyte such as electrode gel 56 which serves to promote the conductivity of electrode isolation means 48 and 49 thereby promoting the conduction and dispersion of the waveform energy to the tissues or organs to be anesthetized.

Knob 34 is positioned on the exterior of the remote control housing 33. Knob 34 operates the internal circuit contained within the remote control housing 33 so as to control the intensity of the waveform and corresponding anesthetic affect. Indicator scale 55 is attached to the exterior of the remote control housing 33, adjacent to knob 34, for referencing the position of the knob 34. Alternatively, l.e.d. 54 may be utilized to indicate intensity through variation in brightness.

Figure 2:
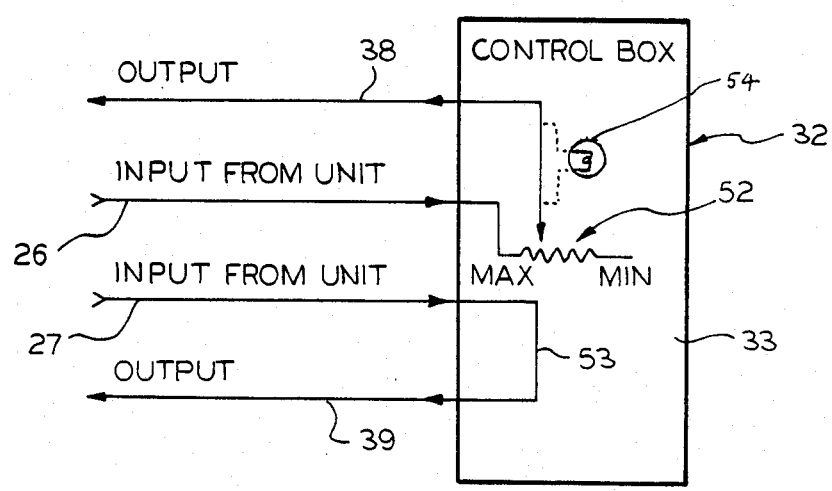
FIG. 2 of the drawings is a schematic circuit diagram showing the electrical structure of the internal circuit control means associated with the dental anesthesia apparatus.

A schematic circuit diagram of the internal circuit which is contained within remote control housing 33, is shown in FIG. 2. The internal circuit means preferably comprises a 0-250 ohm rheostat element 52 which is connected between one of the incoming leads 26 and one of the outgoing leads 38. A conductor element 53 is connected in series, creating a short circuit, between the other incoming lead 27 and the other outgoing lead 39. Knob 34, of FIG. 1, is connected to rheostat element 52 to adjust the resistance of rheostat element 52. When the resistance of rheostat element 52 is at a minimum, corresponding substantially to zero ohms, the intensity of the waveform being conducted through the dental anesthesia apparatus 32, and corresponding anesthetic affect of the waveform are at a maximum. When the resistance of rheostat element 52 is at a maximum, corresponding substantially to 250 ohms, the intensity of the wave form being conducted through the dental anesthesia apparatus 32 and corresponding anesthetic affect of the wave form are at a minimum. Scale 55 positioned on the exterior of remote control housing 33, or alternatively variable l.e.d. 54 integrated into the circuit of FIG. 2 reflects this range and effect.

The foregoing description and drawings merely explain and illustrate the invention and the invention is not limited thereto, except insofar as the amended claims are so limited as those skilled in the art who have the disclosure before them will be able to make modifications and variations therein without departing from the scope of the invention.

What is claimed is:

1. A dental anesthesia apparatus for use with transcutaneous electrical nerve stimulation equipment of the type capable of generating a low energy electrical impulse wave for direct transmission of said impulse wave to the tissues or organs of a patient to lessen discomfort and relieve pain, and in which said transcutaneous electrical nerve stimulation equipment is of the type further including wave generation means to produce a desired waveform, wave control means for independently varying the frequency of said waveform and wave output means to accept, in a facilitated manner, electrical connection of said dental anesthesia apparatus toward direct controllable transmission of said generated electrical impulse wave toward the further relief of pain and lessening of discomfort arising from dental problems and dental procedures directed thereto; said dental anesthesia apparatus comprising:

apparatus connection means for operably and electrically connecting dental anesthesia apparatus to said transcutaneous electrical nerve stimulation equipment, said apparatus connection means having a first end and a second end positioned immediately opposite said first end, said first end for electrical connection to said wave output means of said transcutaneous electrical nerve stimulation equipment so as to be capable of conducting said waveform produced by said wave generation means to said dental anesthesia apparatus, incoming lead means having a first end and a second end, said first end operably and electrically connected to said second end of said apparatus connection means, said incoming lead means serving to further operably and electrically connect said dental anesthesia apparatus to said transcutaneous electrical nerve stimulation equipment, so as to further conduct the waveform produced thereby for use in said dental procedures, internal circuit control means connected to said incoming lead means at a first end, for electrically altering, at a location remote to said transcutaneous electrical nerve stimulation equipment, the intensity of the waveform produced by said wave generation means being conducted through said dental anesthesia apparatus, said incoming lead means further being flexible to permit said internal circuit control means to be reorientatable for its facilitated use by said patient in a position completely remote to and independently operable from said wave generation means to permit said patient to alter the intensity of said waveform in response to the degree of pain experienced by said patient undergoing said dental procedure to enable said patient to, without assistance, control the anesthetic effect generated by said electrical impulse wave, directly and solely to said patient's oral tissue and membranes where said pain and discomfort arises, outgoing connector means having a first end and a second end, said first end operably and electrically connected to said second end of said internal circuit control means, remote control housing means for operably containing and housing said incoming connector means, said outgoing connector means and said internal circuit control means, flexible outgoing lead means having a first end and a second end reorientatable relative to said first end, said first end operably and electrically connected to the second end of said outgoing connector means for further conducting the waveform as controlled by said internal circuit control means, at least two electrode connector means operably and electrically connected to the second end of said outgoing lead means and flexibly reorientation relative to each other, electrode means operably and electrically connected to each of said at least two electrode connector means for selectable and maintainable positioning in said patient's mouth during a dental procedure and for conducting and disbursing said controlled waveform to the area of tissue or organ to be anethetized, said electrode means including a plurality of independently separable means wholly positionable within said patient's mouth for providing a complete electrical circuit therebetween and entirely within said patient's mouth, without creating an electrical circuit across portions of the patient's body external to said oral tissue and membranes thereby forming a closed path for the flow of said waveform to limit the flow of electrical energy of said waveform to the specific desired areas of said oral tissue and membranes to be anesthetized within said mouth, electrode isolation means for isolating said electrode means so as to prevent said electrode means from directly contacting oral tissue and membranes to be anesthetized as well as the patient's teeth, electrolyte means impregnated into said electrode isolation means for effectively disbursing said waveform energy to the tissue or organ to be anesthetized.

2. The invention according to claim 1 in which said apparatus connection means comprises a pair of single conductor male banana jack connectors for the facilitated telescopic and electrical connection of said first end of said incoming lead means with said wave output means of said transcutaneous electrical nerve stimulation equipment, said wave output means including a pair of corresponding single conductor female banana jack connectors.

3. The invention according to claim 1 in which said incoming lead means comprises a pair of single insulated conductor cords having a first end and a second end, said incoming lead means being of such length so as to permit the manual remote operation of said internal circuit control means by an individual proximate to said dental procedure, thereby adjusting the intensity of the waveform and corresponding anesthetic effect, remote from said transcutaneous electrical nerve stimulation equipment by one of an individual performing the dental procedure and the patient.

4. The invention according to claim 1 in which said internal circuit control means comprises a 0-250 ohm rheostat element connected in series between one of said incoming connector means and one of said outgoing connector means and a conductor element connected in series, creating a short circuit, between the other of said incoming connector means and the other of said output connector means, said internal circuit control means serving to electrically alter the intensity and corresponding anesthetic effect of the waveform being conducted through said remote control means, said internal circuit control means further including a knob means by which said rheostat element can be controlled so as to vary the resistance of said rheostat element and an indicator scale positioned on the exterior of said remote control housing means adjacent to said knob means.

5. The invention according to claim 1 in which said outgoing connector means comprises a single two conductor male and female sub-minature phone jack connector assembly for the facilitated telescopic and electrical connection of said internal circuit control means to said outgoing lead means.

6. The invention according to claim 5 in which said outgoing lead means comprises a pair of single conductor cords having said single two conductor male sub-minature phone jack connector operably and electrically attached to said first end of said outgoing lead means for the facilitated telescopic and electrical connection with said corresponding two conductor female sub-minature phone jack connector of said internal circuit means thereby serving to conduct said controlled waveform to said electrode connection means.

7. The invention according to claim 6 in which said outgoing lead means is composed of biomedical wire having a non-toxic Teflon insulation coating capable of undergoing autoclave sterilization without detrimental effect.

8. The invention according to claim 7 in which each of said electrode connector means comprises socket means operably and electrically attached to each conductor of said second end of said outgoing lead means for operably receiving and electrically connecting said outgoing lead means to said electrode means for conducting said controlled waveform to the area of tissue or organ to be anesthetized, said electrode connector means further including an insulating sleeve means covering said socket means so as to prevent the socket means from inadvertent and undesired contact with the tissue, organ or teeth of the patient being anesthetized.

9. The invention according to claim 8 in which said insulating sleeve means is formed of a heat shrinkable teflon tubing material.

10. The invention according to claim 9 in which said socket means is composed of a coiled spring assembly capable of restrainably retaining said electrode means and alternately permitting the removal and replacement of said electrode means.

11. The invention according to claim 1 in which each of said electrode means comprises a tapered stainless steel element for conducting said waveform as controlled by said internal circuit control means and for disbursing said controlled waveform to the area of tissue or organ to be anesthetized.

12. The invention according to claim 11 in which each of said tapered stainless steel elements further includes barbs operably attached thereto so as to retain same within said electrode isolation means.

13. The invention according to claim 11 in which said electrode isolation means operably and telescopically receives said tapered stainless steel elements, said electrode isolation means being firmly retained about said tapered stainless steel elements, said electrode isolating means serving to isolate said stainless steel elements so as to prevent their direct contact with the tissue or organ to be anethetized or the patient's teeth, and further serving to hold said tapered stainless steel elements in place during said dental procedure, said electrode isolation means being dimensioned so as to enable said tapered stainless steel elements to be fully inserted into said electrode isolation means so as to leave no portion of said steel element exposed thereabout.

14. The invention according to claim 13 in which said electrode isolation means comprises an absorbent sponge element.

15. The invention according to claim 1 in which said electrolyte means comprises an electrode gel which, upon impregnation by said electrode isolation means, serves to promote the conductivity of said electrode isolation means so as to maximize the amount of the waveform energy being conducted and dispersed to the tissue or organs being anesthetized.

16. The invention according to claim 1 in which said dental anesthesia apparatus further includes variable visual indicator means comprising a light emitting diode element operably attached to said internal circuit control means, whose degree of variable brightness varies with the intensity of the waveform being conducted through said internal circuit means.

* * * * *

UNITED STATES PATENT AND TRADEMARK OFFICE
CERTIFICATE OF CORRECTION

PATENT NO. : 4,676,257
DATED : June 30, 1987
INVENTOR(S) : Gregory J. Halpern

It is certified that error appears in the above-identified patent and that said Letters Patent is hereby corrected as shown below:

Col. 8, line 41      "reorientation" should be instead -- reorientatable --

Col. 8, line 49      "anethetized" should be instead -- anesthetized --

Col. 10, line 36      "anethetized" should be instead -- anesthetized --

Signed and Sealed this

Tenth Day of November, 1987

Attest:

DONALD J. QUIGG

Attesting Officer     Commissioner of Patents and Trademarks